ics, vol. 7, Issue 1, Sep. 12, 2021, pp. 1-9.
United States Patent
Wang et al.

(10) Patent No.: US 12,399,147 B2
(45) Date of Patent: Aug. 26, 2025

(54) CORONAVIRUS DETECTION METHOD

(71) Applicant: National Tsing Hua University, Hsinchu (TW)

(72) Inventors: Yu-Lin Wang, Hsinchu (TW); Akhil Kavanal Paulose, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 883 days.

(21) Appl. No.: 17/586,782

(22) Filed: Jan. 28, 2022

(65) Prior Publication Data
US 2023/0243776 A1    Aug. 3, 2023

(51) Int. Cl.
*G01N 27/414* (2006.01)
*G01N 33/487* (2006.01)

(52) U.S. Cl.
CPC ..... *G01N 27/4145* (2013.01); *G01N 27/4148* (2013.01); *G01N 33/48714* (2013.01)

(58) Field of Classification Search
CPC .................................................. G01N 27/4145
See application file for complete search history.

(56) References Cited

U.S. PATENT DOCUMENTS

| | | |
|---|---|---|
| 2019/0033251 A1 | 1/2019 | Huang et al. |
| 2019/0154687 A1 | 5/2019 | Sugizaki |
| 2021/0003528 A1 | 1/2021 | Esquivel-Upshaw et al. |

FOREIGN PATENT DOCUMENTS

| | | |
|---|---|---|
| CN | 111148991 | 5/2020 |
| CN | 113549708 | 10/2021 |
| JP | 2016522676 | 8/2016 |
| TW | 201706598 | 2/2017 |
| TW | 201827818 | 8/2018 |
| TW | 202107079 | 2/2021 |
| TW | 202142864 | 11/2021 |

OTHER PUBLICATIONS

Sung D, Koo J. A review of BioFET's basic principles and materials for biomedical applications. Biomed Eng Lett. Apr. 9, 2021;11(2):85-96. (Year: 2021).*
Sarangadharan et al. Single Drop Whole Blood Diagnostics: Portable Biomedical Sensor for Cardiac Troponin I Detection. Anal Chem. Feb. 20, 2018;90(4):2867-2874. (Year: 2018).*
Welch et al. Analysis of Inactivation of SARS-CoV-2 by Specimen Transport Media, Nucleic Acid Extraction Reagents, Detergents, and Fixatives. J Clin Microbiol. Oct. 21, 2020;58(11):e01713-20. (Year: 2020).*
Poghossian A, Jablonski M, Molinnus D, Wege C, Schoning MJ. Field-Effect Sensors for Virus Detection: From Ebola to SARS-CoV-2 and Plant Viral Enhancers. Front Plant Sci. Nov. 24, 2020;11:598103. (Year: 2020).*
Klinghammer et al. Nanosensor-Based Real-Time Monitoring of Stress Biomarkers in Human Saliva Using a Portable Measurement System. ACS Sens. Dec. 24, 2020;5(12):4081-4091. (Year: 2020).*
Seo et al. Rapid Detection of COVID-19 Causative Virus (SARS-CoV-2) in Human Nasopharyngeal Swab Specimens Using Field-Effect Transistor-Based Biosensor. ACS Nano. Apr. 28, 2020;14(4):5135-5142. (Year: 2020).*
"Office Action of Taiwan Counterpart Application", issued on Jan. 8, 2024, p. 1-p. 5.
Akhil K. Paulose et al., "A Rapid Detection of COVID-19 Viral RNA in Human Saliva Using Electrical Double Layer-Gated Field-Effect Transistor-Based Biosensors", Advanced Materials Technologies, vol. 7, Issue 1, Sep. 12, 2021, pp. 1-9.
Pin-Hsuan Chen et al., "Saliva-based COVID-19 detection: A rapid antigen test of SARS-CoV-2 nucleocapsid protein using an electrical-double-layer gated field-effect transistor-based biosensing system" ,Sensors and Actuators: B. Chemical, Jan. 2022, p. 1-11.
"Office Action of Taiwan Counterpart Application", issued on Dec. 28, 2022, p. 1-p. 12.

* cited by examiner

*Primary Examiner* — Nicole Kinsey White
*Assistant Examiner* — Ruixue Wang
(74) *Attorney, Agent, or Firm* — JCIPRNET (57) ABSTRACT

Provided is a coronavirus detection method which is suitable for a coronavirus disease 2019 (COVID-19) detection. The method includes the following steps. A field-effect transistor-based biosensor (BioFET) platform is provided, wherein the BioFET platform includes a BioFET and a sensor card. The sensor card is detachably connected to the BioFET, wherein the sensor card includes a plurality of sensors and each of the plurality of sensors includes a response electrode. A nucleic acid probe specific to a nucleic acid sequence of COVID-19 virus is immobilized on a surface of the response electrode. A test solution is placed on the response electrode of the sensor card. A pulse voltage is applied to the response electrode, and a detection current generated from the sensor card is measured.

8 Claims, 4 Drawing Sheets
Specification includes a Sequence Listing.

FIG. 5

CORONAVIRUS DETECTION METHOD

TECHNICAL FIELD

The invention is related to a method of detecting coronavirus, and more particularly, to a method of detecting coronavirus disease 2019 (COVID-19).

BACKGROUND

Coronavirus disease 2019 (COVID-19) is an infectious disease caused by the severe acute respiratory syndrome coronavirus 2 (SARS-CoV-2). The epidemiology reports, released by the World Health Organization, confirmed that the spread of the coronavirus disease 2019 (COVID-19) has reached over 177 million people as of late June, 2021. With such a swift outspread and an escalating mortality, an effective tool should be implemented for accurate diagnoses, early detection, and disease control.

Several techniques are currently being deployed to address an increased demand for rapid screenings: for example, i) real-time reverse-transcription polymerase chain reaction (real-time RT-PCR); ii) reverse transcription loop-mediated isothermal amplification (RTLAMP); iii) lateral flow assays; and iv) enzyme-linked immunosorbent assay (ELISA).

Real-time RT-PCR is the primary method used for nucleic acid-based detection, while COVID-19 sample collection majorly relies on nasal swabs that is particularly uncomfortable for examinees. Furthermore, the process is time-consuming (turnaround time: ≈24 h), and the test requires highly-trained professionals to operate in centralized laboratories, limiting the number of tests measured in a single run.

SUMMARY

The invention provides a method of detecting coronavirus, suitable for the detection of the coronavirus disease 2019 (COVID-19), and has the characteristics of convenience, rapid, accuracy and low cost.

A method of detecting the coronavirus of the invention is suitable for the detection of the coronavirus disease 2019 (COVID-19). The detection method of COVID-19 included the following steps. A field-effect transistor-based biosensor (BioFET) platform is provided, wherein the BioFET platform includes a BioFET and a sensor card. The sensor card is detachably connected to the BioFET, wherein the sensor card includes a plurality of sensors and each of the plurality of sensors includes a response electrode. A nucleic acid probe specific to a nucleic acid sequence of COVID-19 virus is immobilized on a surface of the response electrode. A test solution is placed on the response electrode of the sensor card. A pulse voltage is applied to the response electrode, and a detection current generated from the sensor card is measured.

In one embodiment of the invention, the BioFET may be an electrical double layer (EDL)-gated field-effect transistor-based biosensor (BioFET) (EDL-gated BioFET).

In one embodiment of the invention, the response electrode may include an input electrode and a gate electrode, wherein the pulse voltage is applied to the input electrode, and the gate electrode is connected to a gate end of the BioFET.

In one embodiment of the invention, a gate end of the BioFET is wire-connected to the sensor card via a gold finger.

In one embodiment of the invention, the nucleic acid probe may include a first nucleic acid probe having a nucleic acid sequence of SEQ ID NO: 1, a second nucleic acid probe having a nucleic acid of SEQ ID NO: 2, a third nucleic acid probe having a nucleic acid sequence of SEQ ID NO: 3 or a combination thereof.

In one embodiment of the invention, the nucleic acid probe is modified by fluorescence.

In one embodiment of the invention, the test solution includes nasal or oropharyngeal secretions treated with a virus lysis buffer.

In one embodiment of the invention, the virus lysis buffer includes a sodium dodecyl sulfate (SDS) solution.

In one embodiment of the invention, before the test solution is placed on the response electrode, further comprising performing a heat treatment on the test solution, wherein a heating temperature of the heat treatment is 90° C. to 100° C., and a heating time of the heat treatment is 3 minutes to 10 minutes.

Based on the above, the method of detecting coronavirus of the invention can demonstrate the ability for rapid COVID-19 viral RNA screening with ease of pretreatment. Furthermore, the BioFET platform used in the detection method of coronavirus of the invention has the extended-gate configuration, which resolves the issues of corrosion and a short lifetime by preventing direct contact between a biological sample and a sensor surface.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

The following disclosure provides many different embodiments, or examples, for implementing different features of the provided subject matter. Specific examples of components and arrangements are described below to simplify the present invention. These are, of course, merely examples and are not intended to be limiting.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Definition of Terms

Unless defined otherwise, all technical and scientific terms used herein have the same meanings as commonly understood by one of ordinary skill in the art to which the invention belongs. Although any methods and materials similar or equivalent to those described herein can be used in the practice or testing of embodiments in accordance with the invention; the methods, devices, and materials are now described. All patents and publications mentioned herein are incorporated herein by reference for the purpose of describing and disclosing the materials and methodologies that are reported in the publications may be used in connection with the present invention.

In the present embodiment, the term "FET," as used herein, refers to a field effect transistor. A type of FET is referred to as a "metal oxide semiconductor field effect transistor" (MOSFET). MOSFETs can be planar structures built in and on the planar surface of a substrate such as a semiconductor wafer. MOSFETs can also have a three-dimensional, fin-based structures.

In the present embodiment, the term "measurement" generally refers to the process of determining the amount, quantity, quality, or property of a target analyte based on its binding to a capture reagent.

In the present embodiment, the term "detection" generally refers to the process of determining the presence or absence of a target analyte based on its binding to a capture reagent. Detection includes but is not limited to identification, measurement, and quantitation.

In the present embodiment, the term "target analyte" as used herein, is the substance to be detected in the test sample using embodiments of the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

In the present embodiment, the term "immobilized," when used with respect to, for example, a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based upon the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

In the present embodiment, the term "nucleic acid" used interchangeably refers to a nucleotide polymer of any length, and includes DNA and RNA. A nucleotide may be a deoxyribonucleotide, a ribonucleotide, a modified nucleotide, or a base and/or an analog thereof, or any matrix that may be incorporated into a polymer by DNA or RNA polymerase. A polynucleotide may include a modified nucleotide, such as a methylated nucleotide and an analog thereof.

In the present embodiment, the term "oligonucleotide" generally refers to a shorter, single-stranded, synthetic polynucleotide, with a length generally not exceeding about 200 nucleotides, but the disclosure is not limited thereto. In the present embodiment, the terms "oligonucleotide" and "polynucleotide" are not mutually exclusive. The above description of a polynucleotide is equally and fully applicable to an oligonucleotide.

In the present embodiment, the terms "5'" and "3'" usually refer to the directional two ends of the same polynucleotide or oligonucleotide in a polynucleotide or oligonucleotide. Generally, 5' is located upstream and 3' is located downstream, and a nucleotide in vivo is synthesized in the 5' to 3' direction.

In the present embodiment, the term "hybridization" means that two nucleic acid molecules must have a high degree of homogeneity between each other (homology), so that a complex is stabilized by hydrogen bonds between the bases of a nucleotide group. In the present embodiment, a part of a nucleic acid molecule may be specifically hybridized with or annealed to a complementary sequence on another nucleic acid molecule. For example, there may be a fragment of an unhybridized nucleotide at the 5'-end of a nucleic acid molecule, and a fragment of a sequence at the 3'-end of the same nucleic acid molecule is specifically hybridized with or annealed to another nucleic acid molecule.

In the present embodiment, in the term of nucleic acid, "denaturation" refers to performing a treatment on a nucleic acid template so that a complementary double-stranded nucleic acid molecule is divided into single-stranded nucleic acid molecules, or the double-stranded structure in a single strand nucleic acid is opened. In the term of protein, "denaturation" refers to the phenomenon that the protein is subjected to certain physical and chemical factors, and its high-order structure is destroyed, thereby losing its biological activity.

In the present embodiment, the term "primer" is usually a shorter single-stranded polynucleotide, and usually has a free 3'-OH group. The primer binds to a target of interest by hybridizing with a target sequence, and then promotes the polymerization of a polynucleotide complementary to the target.

In the present embodiment, the term "amplification" refers to the process of producing two or more copies of a desired sequence. The components of the amplification reaction may include a primer, a nucleic acid template, a polymerase, a nucleotide, and a dNTP, but the disclosure is not limited thereto.

Figure 1:
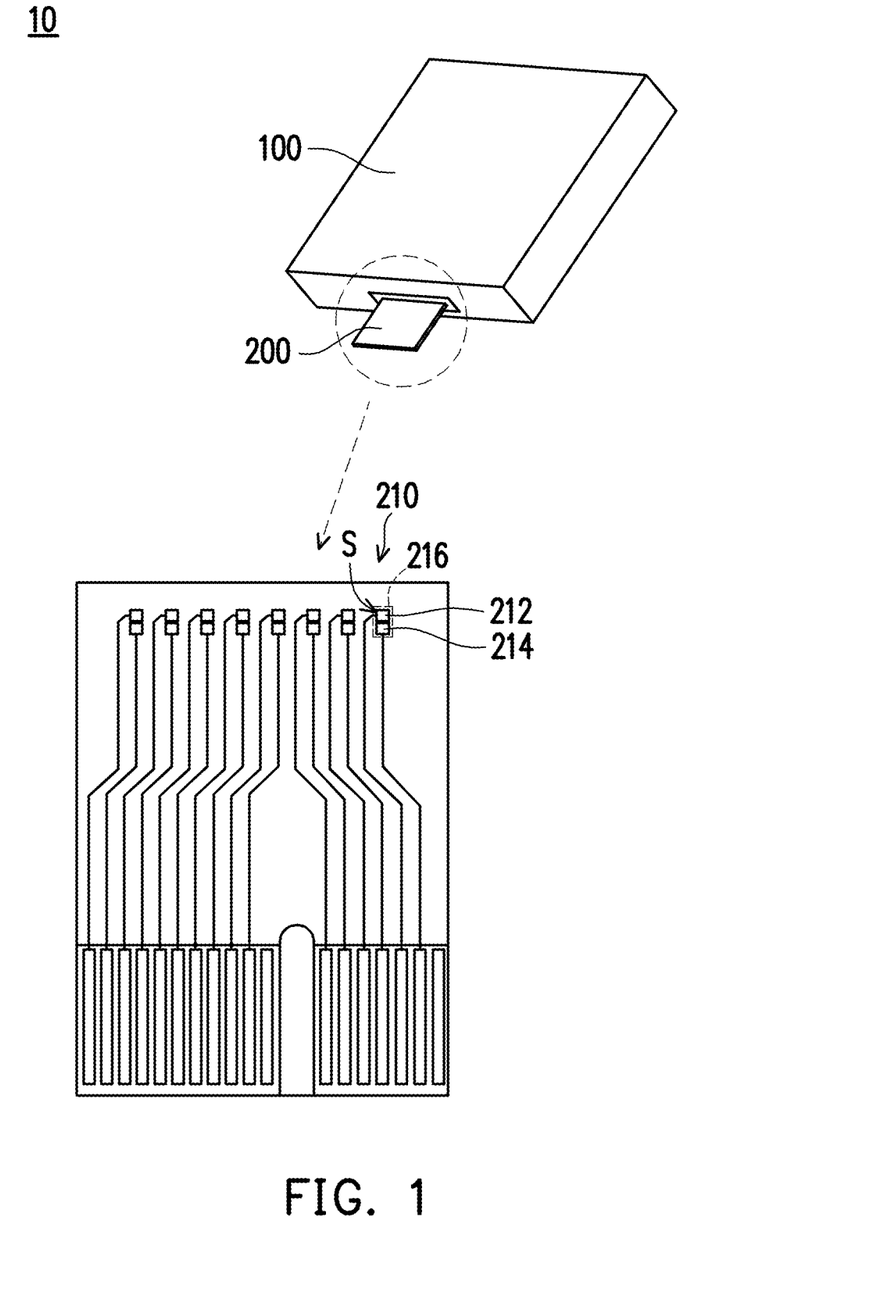
FIG. 1 is a schematic diagram of a BioFET platform according to an embodiment of the invention.

FIG. 1 is a schematic diagram of a BioFET platform according to an embodiment of the invention.

Referring to FIG. 1, the field-effect transistor-based biosensor (BioFET) platform 10 includes a BioFET 100 and a sensor card 200. The BioFET 100 may include a plurality of field-effect transistors to detect the sensing signal. In the present embodiment, the BioFET 100 may be a portable reader.

In the present embodiment, the BioFET 100 is, for instance, an electrical double layer (EDL)-gated field-effect transistor-based biosensor (BioFET) (EDL-gated BioFET). The use of the EDL-gated BioFE can avoid the Debye screening effect and enable detection in a physiological condition. The sensing modality of the EDL-gated BioFET is predicated on EDL capacitance and non-faradic effect, resulting in an ease of sample pretreatment.

The sensor card 200 is detachably connected to the BioFET 100. In the present embodiment, the BioFET platform 10 has the extended-gate configuration, and the gate end of the BioFET 100 is wire-connected to the detachable sensor card 200 via a gold finger. The extended-gate configuration resolves the issues of corrosion and a short lifetime by preventing direct contact between a biological sample and a sensor surface.

The sensor card 200 includes a plurality of sensors 210 spaced apart from each other. In one embodiment, the plurality of sensors 210 are arranged in a array. In the FIG. 1, the sensor card 200 includes 8 individually addressable sensors 210 arranged in a 1×8 array. The number and arrangement of the sensors 210 shown in FIG. 1 are only for exemplary purpose, and are not intended to limit the disclosure. In other embodiments, the arrangement and the number of the sensors 210 may be changed according to requirements.

Each of the sensors 210 includes a response electrode 212, and the response electrode 212 is is formed by a metal material. The material of the response electrode 212 is selected from materials that can be bonded to a subsequently-selected nucleic acid probe. In the present embodiment, the material of the response electrode 212 is, for instance, gold.

In the present embodiment, the response electrode 212 includes a pair of electrodes. More specifically, the response electrode 212 includes a input electrode 214 and a gate electrode 216. The input electrode 214 is applied a pulse voltage (i.e. gate voltage $V_g$). In the present embodiment, the gate electrode 216 acts as the extended gate electrode and is connected to the gate end of the BioFET 100. In the present embodiment, a sensing area (not illustrated) on each electrode is defined by photolithography. Moreover, during the measurement, the source end of the BioFET 100 ($V_s$) is grounded and a drain voltage ($V_D$) is applied to the drain end of the BioFET 100.

In the present embodiment, the surface of the response electrode 212 is immobilized with a nucleic acid probe specific to the COVID-19 virus sequence, wherein the nucleic acid probe may be specifically bonded to the target nucleic acid to be tested. In the present embodiment, the nucleic acid probe may be a single-strand DNA probe. In the present embodiment, the nucleic acid probe may include a first nucleic acid probe having a nucleic acid sequence of SEQ ID NO: 1, a second nucleic acid probe having a nucleic acid of SEQ ID NO: 2, a third nucleic acid probe having a nucleic acid sequence of SEQ ID NO: 3 or a combination thereof. In the present embodiment, the nucleic acid probe is modified by fluorescence, so that the nucleic acid prob has labeling characteristics such as light emission.

In the present embodiment, the BioFET platform 10 may further includes a user interface module (not illustrated), the user interface module may be connected to the BioFET 100. The BioFET 100 can transmit the measured detection current (or sensing signal) to the user interface module.

In the present embodiment, the sensor card 200 includes a plurality of sensor 210, and the plurality of sensor 210 correspond to a same BioFET 100. As a result, the BioFET 100 can perform a plurality of tests on a test solution S at the same time, which not only can increase the reliability of the test result, but can also reduce the time needed for the test. Moreover, since the sensor card 200 is detachable, and only the used sensor card 200 need to be replaced to perform the next test, the cost for the test can be reduced.

The invention also provides a method of detecting coronavirus using the BioFET platform above. Next, the method of detecting coronavirus of the invention is described via the BioFET platform 10 shown in FIG. 1.

Figure 2:
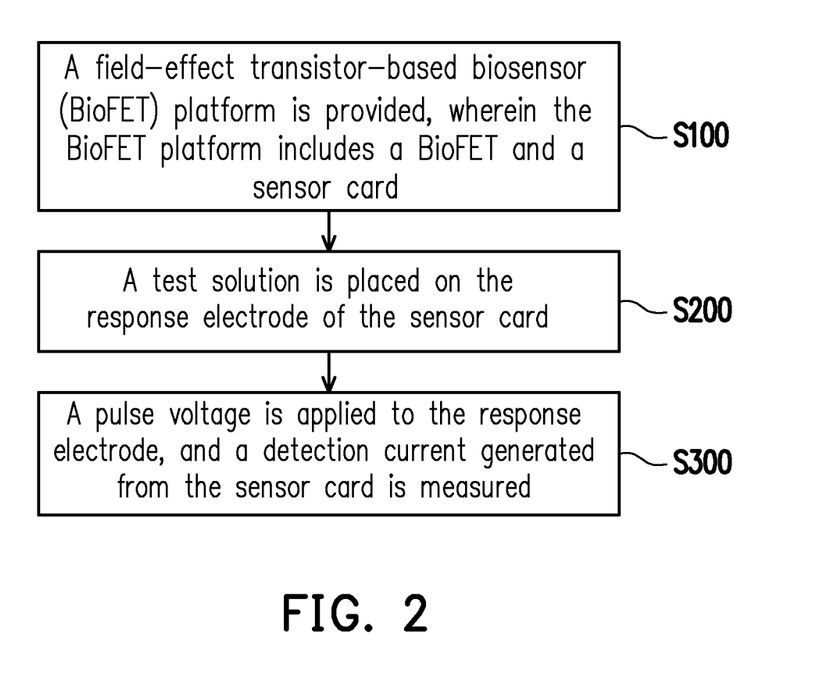
FIG. 2 is a flowchart of a method of detecting coronavirus according to an embodiment of the invention.

FIG. 2 is a flowchart of a method of detecting coronavirus according to an embodiment of the invention.

First, step S100 is performed: providing the BioFET platform, wherein the BioFET platform includes a BioFET and a sensor card. In the present embodiment, the BioFET platform 10 in FIG. 1 is used, for example. The structure related to the BioFET platform 10 are described in detail in the above embodiments, and will not be repeated herein.

Then, the step S110 is performed: placing a test solution on the response electrode of the BioFET. In one embodiment, the test solution may include a medium. The medium may include Tris(hydroxymethyl)aminomethane-Ethylenediaminetetraacetic acid (Tris-EDTA) buffer solution (TE buffer), diethyl pyrocarbonate (DEPC)-treated water, nasal secretions, oropharyngeal secretions or sodium dodecyl sulfate (SDS) solution or a combination thereof, but the invention is not limited thereto. In one embodiment, the test solution may include nasal or oropharyngeal secretions treated with a virus lysis buffer. In one embodiment, the virus lysis buffer may include a SDS solution. In one embodiment, the test solution may be the SDS-treated saliva from the COVID-19 patients. SDS is a surfactant commonly used for lysing a viral envelope and intervening in a nucleic acid-protein interaction by denaturing the protein.

In the present embodiment, the test solution may include a target nucleic acid. In one embodiment, target nucleic acid may be, for instance, a cDNA or RNA having a partial nucleic acid sequence of COVID-19 virus. In one embodiment, the target nucleic acid may be, for instance, COVID-19 viral RNA. In the present embodiment, the test solution is directly contact with the nucleic acid probe on the response electrode, and the target nucleic acid in the test solution may be specifically hybridized with the nucleic acid probe.

In one embodiment, before the test solution is placed on the response electrode (step S200), a heat treatment is performed on the test solution to denature the target nucleic acid into single strands, thereby preventing the target nucleic acid from producing a secondary structure. A heating temperature of the heat treatment may be 90° C. to 100° C., and a heating time of the heat treatment may be 3 minutes to 10 minutes.

Next, the step S300 is performed: applying a pulse voltage to the response electrode, and measuring a detection current generated by the sensor card.

Specifically, after a fixed voltage (i.e. drain voltage $V_D$) is provided to a drain end of the BioFET, a pulse voltage (i.e. gate voltage $V_g$) is applied to the response electrode to generate a voltage difference between the response electrode and the gate end of the BioFET. Therefore, when the target nucleic acid is specifically bonded to the corresponding nucleic acid probe, a capacitance effect occurs between the response electrode and the gate end of the BioFET via the voltage difference generated by applying the pulse voltage to obtain a current value contributed by the capacitance effect. More, specifically, a specific binding of nucleic acid probe/ target nucleic acid caused an electrical redistribution in EDL capacitance, leading to the change of BioFET drain current (i.e. detection current).

In the following, the method of detecting coronavirus and properties thereof provided by the invention are described in detail via experimental examples, but the following experimental examples are not intended to limit the invention. Moreover, the "signal" (gain value) in the experimental examples below represents the difference between a balance current value and an initial current value (i.e., background current) (i.e., balance current value-initial current value=gain value). The initial current value can represent the current value obtained by applying an initial voltage to the response electrode. In the present embodiment, the initial voltage can be less than the gate voltage, but the invention is not limited thereto. The balance current value can represent the current value obtained by applying a gate voltage Vg to the response electrode for a certain period of time.

EXAMPLE

[BioFET Platform]

In the present embodiment, the BioFET platform 10 (including the EDL-gated BioFET and the sensor card) of FIG. 1 is used and the coronavirus detection is performed according to the coronavirus detection steps illustrated in FIG. 2. A sensor card consists of 8 individually addressable sensors arranged in a 1×8 array. The sensing area on each electrode is 500×500 µm².

In the present embodiment, three primer sequences, used in RT-PCR by Taiwan Centers for Disease Control (TCDC), are used as probes (DNA probe 1, DNA probe 2 and DNA probe 3). The details of the three DNA probes are listed below:

```
DNA PROBE 1:
                                        (SEQ ID NO: 1)
5'-TTTTTTGGCAATGTTGTTCCTTGAGGAAGT-3'

DNA probe 2:
                                        (SEQ ID NO: 2)
5'-TTTTTTGTGTAACCGTGGGCGTTAG-3'

DNA probe 3:
                                        (SEQ ID NO: 3)
5'-TTTTTTGAGGAACGAGAAGAGGCTTG-3'
```

A fluorescent dye, 6-carboxyfluorescein (6-FAM), was attached at the 3' end of these sequences (3'FAM) where the dye-tagged complex was excited by a fluorescence microscope and emitted a characteristic color in green. Then, the three DNA probes are immobilized on the surface of the response electrode.

In the present embodiment, the BioFET includes 8 N-channel depletion-mode MOSFETs, which are used to measure sensing signals.

[Measurement Conditions of the BioFET]

In the present embodiment, source and drain properties were measured and recorded using an Agilent B1530/B1500A semiconductor parameter analyzer. A pulse of a 4-ms duration was applied at Vg=0 V and Vg=1 V with a constant drain source voltage (Vd=2 V)

In the present embodiment, the testing solution is drop-casted on the response electrode of the sensor card, covering all the sensing areas. A signal was read out every 2 min, and 11 measurements are taken for each concentration of the analyte.

When a response electrode is functionalized with DNA probes, the surface charge gets redistributed. The EDL capacitance and the potential change across a test solution, due to the probe functionalization, are formed. Furthermore, the output of drain current is measured accordingly by a potential change at the extended electrode. Likewise, the surface charge is redistributed again after the DNA probe-target nucleic acid hybridization, and the corresponding voltage drop/increase is reflected on a BioFET signal.

[Medium and Target Nucleic Acid]

In the present embodiment, three cDNA strands (DNA-1, DNA-2, and DNA-3), and COVID-19 N-gene viral RNA (1260 bases; SEQ ID NO: 7) are used as target nucleic acid for subsequent assays, wherein COVID-19 N-gene viral RNA is complementary to the DNA probes 1-3. In addition, COVID-19 S-gene viral RNA (1108 bases; SEQ ID NO: 8) is used as a negative control, wherein COVID-19 S-gene viral RNA is non-complementary to the DNA probes 1-3. The three sequences of the cDNAs are listed below:

```
DNA-1 (complementary to the DNA probe 1):
                                        (SEQ ID NO: 4)
5'-GCTACAACTTCCTCAAGGAACAACATTGCCAAAAGGCTTCTACGCAG
AAG-3'

DNA-2 (complementary to the DNA probe 2):
                                        (SEQ ID NO: 5)
5'-CCAAAAGATCACATTGGCACCCGCAATCCTGCTAACAATGCTGCAAT
CGT-3'

DNA-3 (complementary to the DNA probe 3):
                                        (SEQ ID NO: 6)
5'-GAGCAGAGGCGGCAGTCAAGCCTCTTCTCGTTCCTCATCACGTAGTC
GCA-3'
```

In the present embodiment, a TE buffer solution, diethyl pyrocarbonate (DEPC)-treated water, human saliva and sodium dodecyl sulfate (SDS)-treated human saliva are used as the medium for the test solution. In the present embodiment, human saliva was collected from COVID-negative individuals by the passive drool method and was stored in −20° C. for the subsequent experiments.

Experimental Example 1 cDNA Detection in Diluted Saliva

In the present embodiment, to reduce the salivary viscosity, the collected saliva was diluted (at a volume ratio of 1:1) with the TE buffer solution. The test solutions (1 fM) with different analytes (DNA-1, DNA-2 and DNA-3) are prepared using diluted saliva.

In the present embodiment, the BioFET reaction is performed using a sensor card immobilized with DNA probe 1. 70 µL of different test solutions are drop-casted and tested (at 25° C.), wherein diluted saliva (without the analyte) is used as control while DNA-2 and DNA-3 are used as the comparative group (non-complementary to DNA probe 1).

Figure 3:
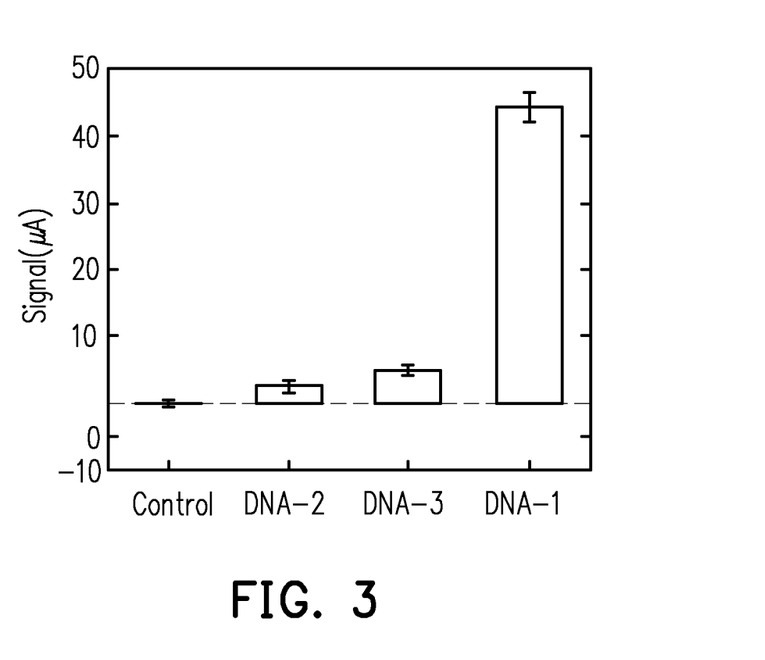
FIG. 3 shows the relationship diagram between the signal and the analyte of experimental example 1.

FIG. 3 shows the relationship diagram between the signal and the analyte of experimental example 1. It can be seen from FIG. 3 that, the analytes of comparative group (DNA-2 and DNA-3) showes signals between 2.43 µA and 4.86 µA, while the signal of the DNA-1 analyte exhibits at least an eightfold increase (44.8 µA). The results indicated that DNA probe 1 enables highly selective probe-target hybridization in human saliva at room temperature.

Experimental Example 2

COVID-19 viral RNA Detection with a 95° C.-Treatment and Comparison of Various Probes In the present embodiment, two different temperatures (25° C. and 95° C.) are used for testing. In the 25° C.-treatment group, the test solutions with different concentrations of target nucleic acid (1 fM, 10 fM, 100 fM and 1 pM; DNA-1, DNA-2 and DNA-3) are prepared using TE buffer. Each kind of DNA probe was immobilized to detect its cDNA (e.g., Probe-1/DNA-1, Probe-2/DNA-2, and Probe-3/DNA-3) in TE buffer solution.

In the 95° C.-treatment group, the test solutions with different concentrations of target nucleic acid (1 fM, 10 fM, 100 fM and 1 pM; COVID-19 N-gene viral RNA) are prepared using diluted saliva.

In the present embodiment, the saliva was diluted (at a volume ratio of 1:1) with the DEPC-treated water to obtain diluted saliva. An addition of DEPC-treated water reduced the risk of RNA degradation.

To avoid the formation of secondary structure at room temperature, the test solutions of the 95° C.-treatment group (RNA samples) are heated for 5 min at 95° C. prior to being drop-casted onto the sensors which are respectively functionalized with DNA probe 1, DNA probe 2, and DNA probe 3 and are detected. The sensors, in the presence of the heated samples, gradually cooled down in 20 min while signals are recorded simultaneously.

Figure 4:
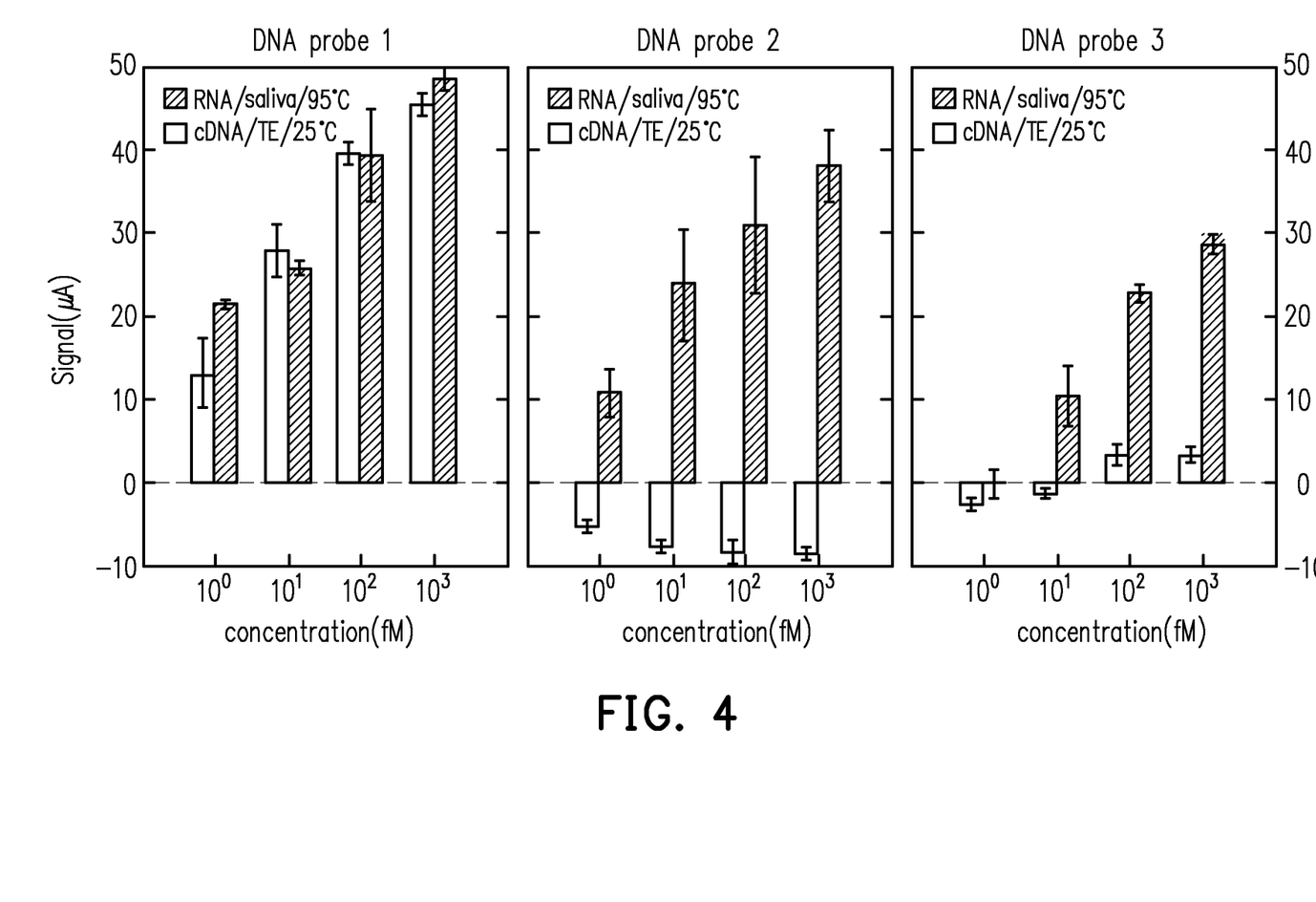
FIG. 4 shows the relationship diagram between the signal and the concentration of experimental example 2.

FIG. 4 shows the relationship diagram between the signal and the concentration of experimental example 2. It can be seen from FIG. 4 that, in the group of DNA probe 1, both RNA and cDNA can be detected with a similar signal response. The ratio of RNA signal to cDNA signal at 1 fm of the nucleic-acid targets is 1.62, while the ratios varies from 0.93 to 1.07 at target concentrations ranging from 10 fM to 1 pM. The trends are significantly different among other probes (i.e. DNA probe 1 and DNA probe 2). The signal ratios of DNA probe-2 varies from −4.43 to −2.03, while DNA probe-3 is unable to capture and detect the cDNA (DNA-3) with a 25° C.-treatment. Compared to RNA detection using DNA probe 1, the group of DNA probe 3 gives rise to the smallest signals (<30 µA) at each concentration while the group of DNA probe 2 exhibits intermediate signals (<38 µA) with the largest uncertainties. We believe that the pairs of DNA probe 2/DNA-2 and DNA probe 3/DNA-3 cannot be obtained at 25° C. due to the formation of secondary structure by which the hybridizations were hindered. As a result, DNA Probe 1 consistently demonstrates the best stability and performance in both cDNA detections with a 25° C.-treatment and COVID-19 viral RNA detections with a 95° C.-treatment.

Experimental Example 3

COVID-19 Viral RNA Detection at Room Temperature and Matrix Insensitivity

To validate rapid COVID-19 screenings for on-site applications, the BioFETs examines RNA samples in various matrices at room temperature.

In the present embodiment, the sensor card immobilized with DNA probe 1 is used to test COVID-19 viral RNAs.

In the present embodiment, COVID-19 S-gene viral RNA serves as a negative control and is tested in diluted human saliva, while COVID-19 N-gene viral RNA is tested with varying media such as diluted human saliva, SDS-treated saliva, and DEPC-treated water.

Figure 5:
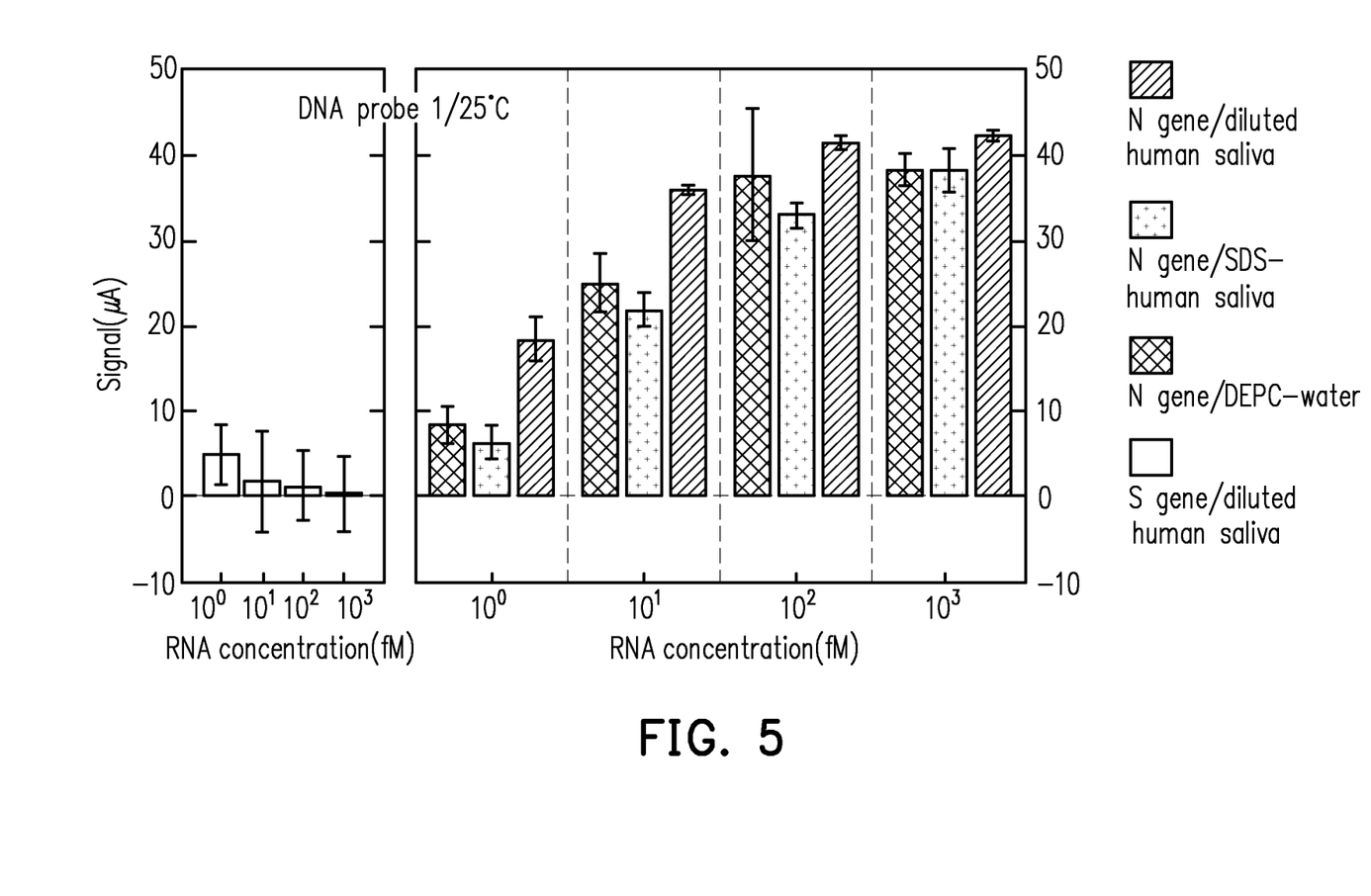
FIG. 5 shows the relationship diagram between the signal and the concentration of experimental example 3.

FIG. 5 shows the relationship diagram between the signal and the concentration of experimental example 3. It can be seen from FIG. 5 that, in the positive group, N-gene RNA demonstrates the highest sensitivity in diluted human saliva, and the signal reaches 42.14 µA at a concentration of 1 pM. As such, the signal obtained from diluted human saliva is taken as the benchmark. Smaller signals are found in DEPC-treated water and SDS-treated saliva, and this trend is more obvious at concentrations of 1 fM making them indistinguishable from the negative control (S-gene RNA). While, at RNA concentrations between 100 fM and 1 pM, the samples of DEPC-treated water exhibit ≈0.9 times the signal amplitude of the diluted human saliva group, and the samples of SDS-treated saliva exhibit 0.8 to 0.9 times the signal amplitude (of the diluted human saliva group). The result indicates the matrix-insensitivity prevailed at the higher concentrations (100 fM-1 pM) when detecting COVID-19 N-gene viral RNA at room temperature; furthermore, the addition of SDS did not affect the signal significantly.

In general, the detection limit in the saliva samples is expectes to pass beyond 1 fM which was the lowest concentration tested in this work, indicating the feasibility to detect viral RNA without PCR processing (i.e., biochemical amplification).

Furthermore, in the present embodiment, the matrix insensitivity is confirmed with the varying media, and the tests performed in SDS and DEPC have similar signal amplitudes compared to what are measured in diluted human saliva. Due to an ease of sample collection/pretreatment, the BioFET platform of the invention can carry out COVID-19 assay within 20 min (total turnaround: ≈1 h). Therefore, the method of detecting coronavirus of the present disclosure is advantageous for COVID-19 assay using saliva due to a high sensitivity, a portable configuration, a label-free operation, and a matrix insensitivity.

Based on the above, the method of detecting coronavirus of the present disclosure can demonstrate the ability for rapid COVID-19 viral RNA screening with ease of pretreatment. Furthermore, the BioFET platform used in the detection method of coronavirus of the present disclosure has the extended-gate configuration, which resolves the issues of corrosion and a short lifetime by preventing direct contact between a biological sample and a sensor surface.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A method of detecting coronavirus, comprising:
providing a field-effect transistor-based biosensor (BioFET) platform, wherein the BioFET platform includes:
a BioFET; and
a sensor card, detachably connected to the BioFET, wherein the sensor card includes a plurality of sensors and each of the plurality of sensors includes a response electrode, wherein a nucleic acid probe specific to a nucleic acid sequence of COVID-19 virus is immobilized on a surface of the response electrode;
placing a test solution on the response electrode of the sensor card; and
applying a pulse voltage to the response electrode and measuring a detection current generated from the sensor card,
wherein the nucleic acid probe includes a first nucleic acid probe having the nucleic acid sequence of SEQ ID NO: 1, a second nucleic acid probe having the nucleic acid of SEQ ID NO: 2, a third nucleic acid probe having the nucleic acid sequence of SEQ ID NO: 3 or a combination thereof.

2. The method of detecting coronavirus of claim 1, wherein the BioFET is an electrical double layer (EDL)-gated field-effect transistor-based biosensor (BioFET).

3. The method of detecting coronavirus of claim 1, wherein the response electrode includes an input electrode and a gate electrode, wherein the pulse voltage is applied to the input electrode, and the gate electrode is connected to a gate end of the BioFET.

4. The method of detecting coronavirus of claim 1, wherein a gate end of the BioFET is wire-connected to the sensor card via the response electrode.

5. The method of detecting coronavirus of claim 1, wherein the nucleic acid probe is modified by fluorescence.

6. The method of detecting coronavirus of claim 1, wherein the test solution includes nasal or oropharyngeal secretions treated with a virus lysis buffer.

7. The method of detecting coronavirus of claim 6, wherein the virus lysis buffer includes a sodium dodecyl sulfate (SDS) solution.

8. The method of detecting coronavirus of claim 1, before the test solution is placed on the response electrode, the method further comprises performing a heat treatment on the test solution, wherein a heating temperature of the heat treatment is 90° C. to 100° C., and a heating time of the heat treatment is 3 minutes to 10 minutes.

* * * * *

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
```

<223> OTHER INFORMATION: DNA probe 1

<400> SEQUENCE: 1
tttttttggc aatgttgttc cttgaggaag t                                    31

<210> SEQ ID NO 2
<211> LENGTH: 25
<212> TYPE: DNA
<213> ORGANISM: Artificial Sequence
<220> FEATURE:
<223> OTHER INFORMATION: DNA probe 2

<400> SEQUENCE: 2 tttttttgtgt aaccgtgggc gttag                                          25

<210> SEQ ID NO 3
<211> LENGTH: 26
<212> TYPE: DNA
<213> ORGANISM: Artificial Sequence
<220> FEATURE:
<223> OTHER INFORMATION: DNA probe 3

<400> SEQUENCE: 3 tttttttgagg aacgagaaga ggcttg                                         26

<210> SEQ ID NO 4
<211> LENGTH: 50
<212> TYPE: DNA
<213> ORGANISM: Artificial Sequence
<220> FEATURE:
<223> OTHER INFORMATION: DNA-1

<400> SEQUENCE: 4
gctacaactt cctcaaggaa caacattgcc aaaaggcttc tacgcagaag                50

<210> SEQ ID NO 5
<211> LENGTH: 50
<212> TYPE: DNA
<213> ORGANISM: Artificial Sequence
<220> FEATURE:
<223> OTHER INFORMATION: DNA-2

<400> SEQUENCE: 5
ccaaaagatc acattggcac ccgcaatcct gctaacaatg ctgcaatcgt                50

<210> SEQ ID NO 6
<211> LENGTH: 50
<212> TYPE: DNA
<213> ORGANISM: Artificial Sequence
<220> FEATURE:
<223> OTHER INFORMATION: DNA-3

<400> SEQUENCE: 6
gagcagaggc ggcagtcaag cctcttctcg ttcctcatca cgtagtcgca                50

<210> SEQ ID NO 7
<211> LENGTH: 1260
<212> TYPE: DNA
<213> ORGANISM: Artificial Sequence
<220> FEATURE:
<223> OTHER INFORMATION: COVID-19 N-gene

<400> SEQUENCE: 7
atgtctgata atggacccca aaatcagcga aatgcacccc gcattacgtt tggtggaccc     60
tcagattcaa ctggcagtaa ccagaatgga gaacgcagtg gggcgcgatc aaaacaacgt    120

| | | |
|---|---|---|
| cggccccaag gtttacccaa taatactgcg tcttggttca ccgctctcac tcaacatggc | 180 |
| aaggaagacc ttaaattccc tcgaggacaa ggcgttccaa ttaacaccaa tagcagtcca | 240 |
| gatgaccaaa ttggctacta ccgaagagct accagacgaa ttcgtggtgg tgacggtaaa | 300 |
| atgaaagatc tcagtccaag atggtatttc tactacctag aactgggcc agaagctgga | 360 |
| cttccctatg gtgctaacaa agacggcatc atatgggttg caactgaggg agccttgaat | 420 |
| acaccaaaag atcacattgg cacccgcaat cctgctaaca atgctgcaat cgtgctacaa | 480 |
| cttcctcaag gaacaacatt gccaaaaggc ttctacgcag aagggagcag aggcggcagt | 540 |
| caagcctctt ctcgttcctc atcacgtagt cgcaacagtt caagaaattc aactccaggc | 600 |
| agcagtaggg gaacttctcc tgctagaatg gctggcaatg gcggtgatgc tgctcttgct | 660 |
| ttgctgctgc ttgacagatt gaaccagctt gagagcaaaa tgtctggtaa aggccaacaa | 720 |
| caacaaggcc aaactgtcac taagaaatct gctgctgagg cttctaagaa gcctcggcaa | 780 |
| aaacgtactg ccactaaagc atacaatgta acacaagctt tcggcagacg tggtccagaa | 840 |
| caaacccaag gaaattttgg ggaccaggaa ctaatcagac aaggaactga ttacaaacat | 900 |
| tggccgcaaa ttgcacaatt tgcccccagc gcttcagcgt tcttcggaat gtcgcgcatt | 960 |
| ggcatggaag tcacaccttc gggaacgtgg ttgacctaca caggtgccat caaattggat | 1020 |
| gacaaagatc caaatttcaa agatcaagtc attttgctga ataagcatat tgacgcatac | 1080 |
| aaaacattcc caccaacaga gcctaaaaag acaaaaaga agaaggctga tgaaactcaa | 1140 |
| gccttaccgc agagacagaa gaaacagcaa actgtgactc ttcttcctgc tgcagatttg | 1200 |
| gatgatttct ccaaacaatt gcaacaatcc atgagcagtg ctgactcaac tcaggcctaa | 1260 |

<210> SEQ ID NO 8
<211> LENGTH: 1108
<212> TYPE: DNA
<213> ORGANISM: Artificial Sequence
<220> FEATURE:
<223> OTHER INFORMATION: COVID-19 S-gene

<400> SEQUENCE: 8

```
atgtttgttt ttcttgtttt attgccacta gtctctagtc agtgtgttaa tcttacaacc     60
agaactcaat tacccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
```

-continued

```
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatata                                      1108
```